(12) United States Patent
Schubert et al.

(10) Patent No.: US 9,782,068 B2
(45) Date of Patent: Oct. 10, 2017

(54) SYSTEM FOR DIAGNOSIS AND THERAPY OF GAZE STABILITY

(75) Inventors: Michael C. Schubert, Parkton, MD (US); Americo A. Migliaccio, Kingsford (AU); Charles Coleman Della Santina, Towson, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 1422 days.

(21) Appl. No.: 12/698,551

(22) Filed: Feb. 2, 2010

(65) Prior Publication Data
US 2010/0198104 A1  Aug. 5, 2010

Related U.S. Application Data

(60) Provisional application No. 61/149,155, filed on Feb. 2, 2009.

(51) Int. Cl.
| | |
|---|---|
| *A61B 13/00* | (2006.01) |
| *A61B 3/113* | (2006.01) |
| *A61B 5/11* | (2006.01) |
| *A61B 5/00* | (2006.01) |

(52) U.S. Cl.
CPC .............. *A61B 3/113* (2013.01); *A61B 5/11* (2013.01); *A61B 5/4863* (2013.01); *A61B 5/4023* (2013.01); *A61B 5/6803* (2013.01); *A61B 5/6814* (2013.01); *A61B 5/6831* (2013.01); *A61B 2562/0219* (2013.01)

(58) Field of Classification Search
CPC ......... A61B 3/113; A61B 5/11; A61B 5/4863; A61B 5/16; A61B 5/162

USPC ............ 600/558, 595; 601/46; 382/103, 100
See application file for complete search history.

(56) References Cited

U.S. PATENT DOCUMENTS

| | | | | |
|---|---|---|---|---|
| 5,984,475 | A | * | 11/1999 | Galiana et al. ............... 351/209 |
| 6,164,134 | A | * | 12/2000 | Cargille ............ G01C 19/5719 |
| | | | | 73/504.02 |
| 8,333,472 | B2 | * | 12/2012 | Kiderman ..................... 351/200 |
| 2006/0005846 | A1 | * | 1/2006 | Krueger et al. .............. 128/898 |

(Continued)

OTHER PUBLICATIONS

Becker, R. et al., "Examination of young children with Lea symbols," Br. J. Ophthalmol. 86:513-516, 2002.
(Continued)

*Primary Examiner* — Daniel Cerioni
(74) *Attorney, Agent, or Firm* — Venable LLP; Henry J. Daley (57) ABSTRACT

A system to improve vestibulo-ocular reflex (VOR) includes a display device; a head motion detector, the head motion detector being configured to detect at least one of a first angular rotational rate of a subject's head or a first acceleration of said subject's head in a first direction; a signal conditioner in communication with the head motion detector; a first gain control in communication with the signal conditioner; a second gain control in communication with the signal conditioner; a motion controller in communication with the display device and the first gain control and the second gain control; and a head motion-inducing device configured to induce a head motion on the subject. The head motion-inducing device includes a motor configured to rotate a head of the subject based on an instruction produced by a data processor.

6 Claims, 8 Drawing Sheets

(56) References Cited

U.S. PATENT DOCUMENTS

| | | | |
|---|---|---|---|
| 2007/0121066 A1* | 5/2007 | Nashner | 351/210 |
| 2009/0058660 A1* | 3/2009 | Torch | 340/573.1 |

OTHER PUBLICATIONS

Della Santina, C.C. et al., "Orientation of Human Semicircular Canals Measured by Three-Dimensional Multiplanar CT Reconstruction," *J. Assoc. Res. Otolaryngol.*, Aug. 9, 2005, pp. 1-16.

Gazzola, J.M. et al., "Circumstances and consequences of falls in elderly people with vestibular disorder," *Rev. Bras. Otorrinolaringol.* 72:(3):388-92, May-Jun. 2006, (English Ed.).

Herdman, S.J. et al., "Recovery of Dynamic Visual Acuity in Unilateral Vestibular Hypofunction," *Arch. Otolaryngol. Head Neck Surg.* 129:819-824, 2003.

National Institutes of Health, National Institute on Deafness and Other Communication Disorders, "A Report of the Task Force on the National Strategic Research Plan," Bethesda, Maryland, Apr. 1989, p. 12.

Scherer, M., et al., "Effect of Vestibular Rehabilitation on Passive Dynamic Visual Acuity," *Journal of Vestibular Research* 18 (2008) 147-157.

Schubert, M.C. et al., "Incremental angular vestibulo-ocular reflex adaptation to active head rotation," *Exp. Brain Res.* 191(4):435-446, 2008b.

Schubert, M.C., et al., "Oculomotor Strategies and Their Effect on Reducing Gaze Position Error," *Otology & Neurology*, 31(2):228-231-00, Feb. 2010.

Schubert, M.C. et al., "Vertical dynamic visual acuity in normal subjects and subjects with vestibular hyperfunction," *Otology & Neurotology* 23:372-377, 2002.

Schubert, M.S. et al., "Dynamic visual acuity during passive head thrusts in canal planes," *J. Assoc. Res. Otolaryngol.* 7(4):329-38, Dec. 2006. Epub Jun. 30, 2006.

Schubert, M.D. et al., "Mechanism of dynamic visual acuity recovery with vestibular rehabilitation," *Arch. Phys. Med. Rehab.* 89:3, Mar. 2008.

Schubert, M.C. et al., "Optimizing the sensitivity of the head thrust test for identifying vestibular hypofunction," *Phys. Ther.* 84(2):151-8, Feb. 2004.

\* cited by examiner

SYSTEM FOR DIAGNOSIS AND THERAPY OF GAZE STABILITY

CROSS-REFERENCE OF RELATED APPLICATION

This application claims priority to U.S. Provisional application Ser. No. 61/149,155 filed Feb. 2, 2009, the entire contents of which are hereby incorporated by reference.

BACKGROUND

1. Field of Invention

The current invention relates to the diagnosis, treatment, and therapy monitoring for vestibule-ocular reflex (VOR) dysfunction.

2. Discussion of Related Art

The vestibular system is integral to balance control. The paired vestibular organs, housed within the temporal bone, include three orthogonal semicircular canals (superior, posterior, and horizontal) and two otolith organs (the utricle and saccule). Together, the semicircular canals and otolith organs provide continuous input to the brain about rotational and translational head motion and the head's orientation relative to gravity. This information from the vestibular organs and their central pathways allows for the maintenance of gaze and postural stability via the vestibulo-ocular reflex and vestibulospinal reflex, respectively. Dysfunction of the peripheral vestibular structures cannot be directly observed but can be inferred from assessment of these reflexes (e.g., with caloric reflex test).

Vestibular dysfunction is typically characterized by vertigo (i.e., an illusory sense of motion) and imbalance owing to disturbances in gaze and postural stability. In some cases, vestibular dysfunction can culminate catastrophically in a fall, which is associated with serious injury and restricted mobility and ranks among the leading causes of death among older individuals. The costs of increased needs and diminished autonomy associated with falls also exert a tremendous societal toll.

Vestibular dysfunction is common among adults in the United States. The National Institute of Health (NIH) estimates that over 90 million Americans, age 17 and older, have experienced a dizziness or balance disorder. Data has established that approximately 53% of patients with inner ear disorders have a costly fall. The non-profit Vestibular Disorders Association reports 37,800 requests per month to locate physicians, physical therapists, and audiologists who specialize in vestibular disorders. The expectation is that balance and dizziness problems in the United States will continue to demand significant hospitalization and treatment costs. These data suggest the importance of diagnosing, treating, and potentially screening for vestibular deficits to reduce the burden of fall-related injuries and deaths in the United States.

The main function of the vestibulo-ocular reflex (VOR) is to stabilize visual images on the retina during head rotations. Gaze stability is defined as the ability to see clearly during head motion, and is the unique function of the VOR. In individuals with a normal VOR, visual acuity during head movements typical of daily activities is similar to that measured with the head stationary. In contrast, individuals with abnormal vestibular (inner ear) systems (reduced VOR) report visual images appear to move when their heads are moving. As a result, individuals with reduced VOR have visual image motion on their retinas, resulting in a degradation of visual acuity during head movements.

Traditional and current commercial products only measure acuity when the subject self-induces a head motion. Traditional and current rehabilitation asks patients to move their head while focusing on targets, in an attempt to improve patients' ability to see clearly during head rotation. Although the effectiveness of the available diagnosis and rehabilitation is established, there is a need in the art for improved diagnosis and rehabilitation for VOR dysfunction.

SUMMARY

Some embodiments of the current invention provide a system to measure a subject's gaze stability, comprising: a display device; a data processor in communication with the display device; a data input device in communication with the data processor; and a motion detector in communication with the data processor, the motion detector being adapted to be worn by the subject under observation, wherein the data processor is configured to cause the display device to display a predetermined visual target based on a motion signal detected by the motion detector, the data processor is adapted to receive information from the data input device concerning a response of the subject in identifying the predetermined visual target, and the data processor is further adapted to generate an output characterizing the subject's gaze stability based on the received information.

Some embodiments of the current invention provide a system to improve a subject's vestibulo-ocular reflex (VOR), comprising a display device; a motion detector; and a motion controller in communication with the display device and the motion detector, wherein the motion controller is adapted to receive information encoding the subject's head motion velocity from said motion detector, and the motion controller is further adapted to configure the display device to display a visual target to the subject such that the visual target moves at a velocity smaller than the subject's head motion velocity and in an opposite direction to the subject's head motion.

Some embodiments of the current invention provide a method to measure a subject's gaze stability, comprising the steps of: (a) externally inducing a head motion in the subject under observation; (b) generating a detected signal corresponding to the subject's head motion using a motion sensor; (c) flashing a predetermined visual target to the subject, the flashing is being trigged based on the detected signal; (d) recording information concerning the subject's response in identifying the predetermined visual target being flashed using a data input device; and (e) generating an output characterizing the subject's gaze stability using the information recorded.

Some embodiments of the current invention provide a method to improve a subject's vestibulo-ocular reflex (VOR), comprising the steps of: (a) inducing the subject's head to move in a first direction at a first velocity; (b) moving a visual target in a second direction opposite to the first direction and at a second velocity while the subject's head is in motion; and (c) having the subject visually fixating on the moving visual target, wherein said second velocity is set lower than said first velocity.

Some embodiments of the invention may comprise a computer-readable medium comprising software, when executed by a computer, causes the computer to receive a detected motion signal corresponding to a motion of a human subject's head from motion detector; cause a display device to display a predetermined visual target based on the detected motion signal; receive information corresponding to a response of the human subject in identifying the predetermined visual target from data input device; and generate an output characterizing a gaze stability of said human subject.

Some embodiments of the invention may comprise a computer-readable medium, comprising software, which software when executed by a computer, causes the computer to receive from a motion detector data encoding a first velocity of a subject's head motion in a first direction; and cause a display device to display a visual target moving in a second direction, opposite to said first direction, and at a second velocity that is lower than said first velocity.

BRIEF DESCRIPTION OF THE DRAWINGS

Further objectives and advantages will become apparent from a consideration of the description, drawings, and examples.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited herein are incorporated by reference as if each had been individually incorporated.

Figure 1:
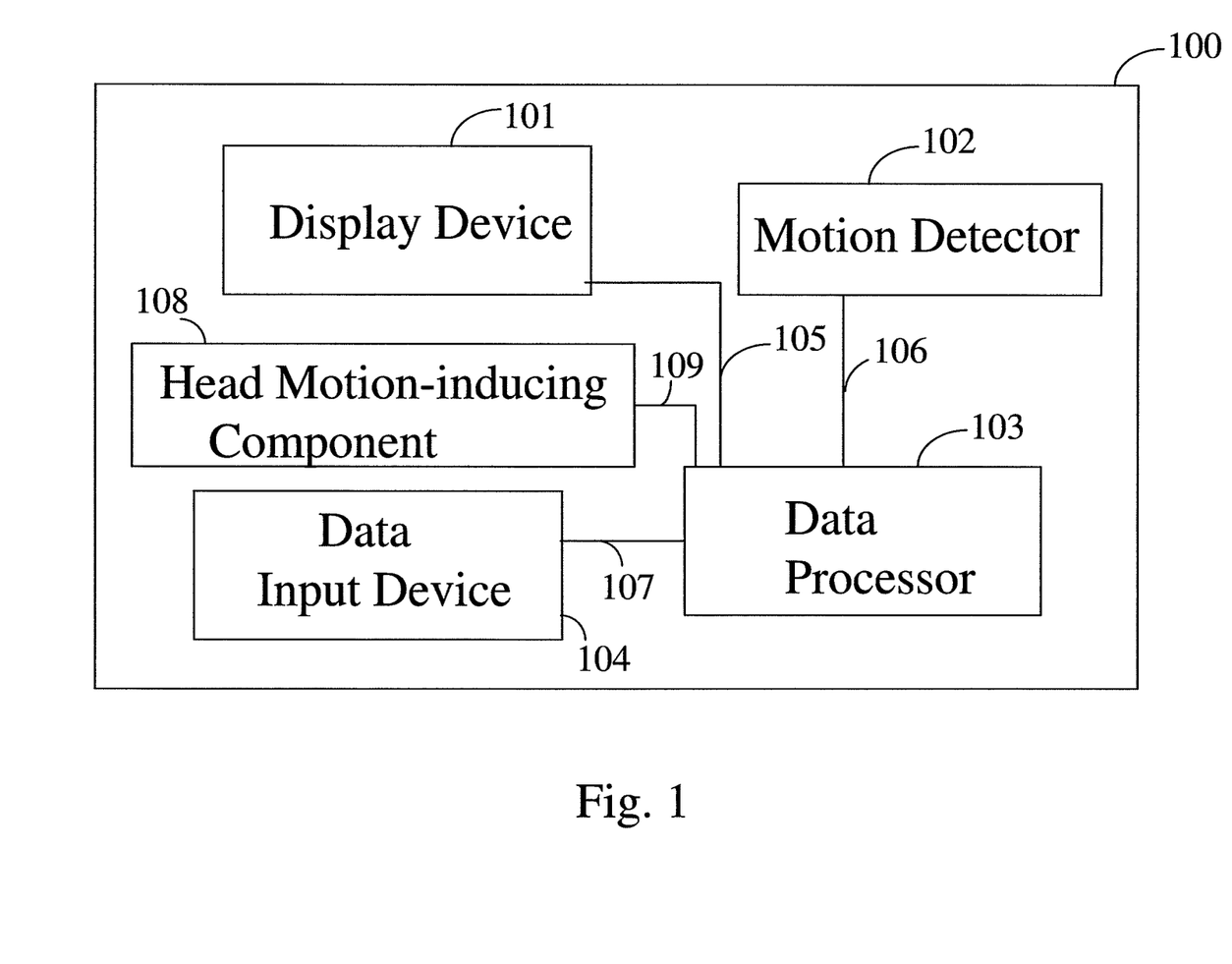
FIG. 1 is a schematic illustration of a system to measure a subject's response in identifying a visual target according to some embodiments of the invention.

FIG. 1 is a schematic illustration of an apparatus to measure a subject's response in identifying a visual target according to some embodiments of the invention. A measurement system 100 may comprise a display device 101, a motion detector 102, a data processor 103, and a data input device 104. Measurement system 100 may further comprise a head motion-inducing component 109.

Data processor 103 may be in communication with display device 101, motion detector 102, and data input device 104 via links 105, 106, and 107 respectively. Data processor 103 may also be in communication with head motion-inducing component 108 via link 109. Links 105 to 107, and 109 may be wired or wireless. A wired link may be, for example, a serial cable, a parallel cable, an Ethernet cable, a USB cable, a firewire cable, a fiber-optic cable, etc. A wireless link may be, for example, a radio-frequency (RF) link based on the Bluetooth or IEEE 802.11 protocols, an infrared link based on the infrared data association (IrDA) specifications. Links 105 to 107, and 109 are not limited to the above particular examples. They can include other existing or future developed communications link without departing from the current invention.

Display device 101 may display a visual target to a human subject. The visual target may be, for example, an optotype character or a letter, and can be displayed in various spatial orientations. The visual target can be flashed. The display device 101 may be, for example, a cathode ray tube (CRT) monitor, a liquid crystal display (LCD) monitor, a digital light projection (DLP) monitor, a projector display, a laser projector, a plasma screen, an organic light emitting diode (OLED), etc. However, display device 101 is not limited to these particular examples. It can include other existing or future developed display devices without departing from the scope of the current invention.

Motion detector 102 may be worn by the human subject, for example, in a head band fit. Motion detector 102 may be, for example, a gyroscopic device that measures the angular rotational rate and acceleration. The gyroscopic device can be piezoelectric or micromechanical. Motion detector 102 can be aligned in such a way that when the head of the human subject is passively rotated in the plane of an individual semicircular canal, function from that particular plane can be determined. Humans have six semicircular canals (SCCs, three in each ear), namely left anterior and right posterior (together comprise the LARP plane); right anterior and left posterior (together comprise the RALP plane); and two horizontal canals (right and left, comprise the horizontal plane). The three SCCs in each ear are orthogonal with each other, and mated with a SCC from the opposite ear (thus, RALP, LARP, horizontal planes). Motion detector 102 may be configured to detection rotations in any one of the three planes. A human examiner may manually rotate the head of the subject in, for example, one horizontal canal while the human subject is asked to identify the visual target being flashed on display device 101. Here, passive rotation means the subject's head rotation is induced externally, for example, by the human examiner. In contrast, active head rotation means the subject's head rotation is self-induced. The subject's head rotation may be induced in a plane of maximal sensitivity of motion detector 102. Motion detector 102, upon detecting the head rotation of the subject may cause the display device 101 to flash the visual target. The visual target may be flashed at several locations in the field of view of the subject at varying levels of acuity, size, and spatial orientation. Thus, a spatial map of the subject's visual acuity may be obtained during head motion. Similarly, another spatial map of the subject's visual acuity when head motion is absent may also be obtained. A difference between the two spatial maps may be a test of the subject's dynamic visual acuity.

Data processor 103 may be in communication with display device 101 and data input device 104 via links 105 and 107, respectively. Data processor 103 may comprise a data storage device, for example, a hard disk drive, a network area storage (NAS) device, a redundant array of independent disks (RAID), a flash drive, an optical disk, a magnetic tape, a magneto-optical disk, etc. However, data storage device is not limited to these particular examples. It can include other existing or future developed data storage devices without departing from the scope of the current invention.

Data processor 103 may be adapted to receive information from data input device 104 and store the information in the data storage device. Data processor 103 may generate an output characterizing the subject's gaze stability based on the stored information. The output may be a spatial map showing the subject's dynamic visual acuity at various locations in the subject's vision. The output may be an index summarizing the subject's dynamic visual acuity. The output may be stored in the data storage device so that the subject's gaze stability can be studied in a longitudinal manner. The longitudinal study can help monitoring, for example, the progress of a therapy for treating gaze stability.

Data processor 103 may be a general purpose computer having a central processing unit (CPU). The computer may be capable of running a software program that may trigger display device 101 to provide a predetermined visual target while receiving a motion signal, detected by motion detector 102, encoding the subject's head motion. Data processor 103 may comprise a logic device configured to receive the detected motion signal of the subject's head motion and trigger display device 101 to flash the predetermined visual target. The logic device may be, for example, a digital processing unit (DSP), a field programmable gated array (FPGA) device, or an application specific device.

Data input device 104 may collect information corresponding to a response of the human subject in identifying the visual target. In one example, data input device 104 may enable the human subject to enter information concerning the perceived visual target. Data input device 104 may be, for example, a microphone, a keyboard, a mouse, or a joystick, etc. For example, a speech recognition system may be employed to process the voice input from the microphone. This information concerning the perceived target may be compared with information concerning the visual targets actually displayed to evaluate the subject's visual acuity.

In another example, data input device 104 may enable a human examiner to enter information concerning the subject's response in identifying the predetermined visual target during an examination. The information concerning the subject's response may be a binary record, for example, either a correct or an incorrect response. The examination may enter the information concerning human subject's responses in identifying predetermined visual targets at different locations, for example, central, peripheral, etc., in the subject's field of view.

Figure 2:
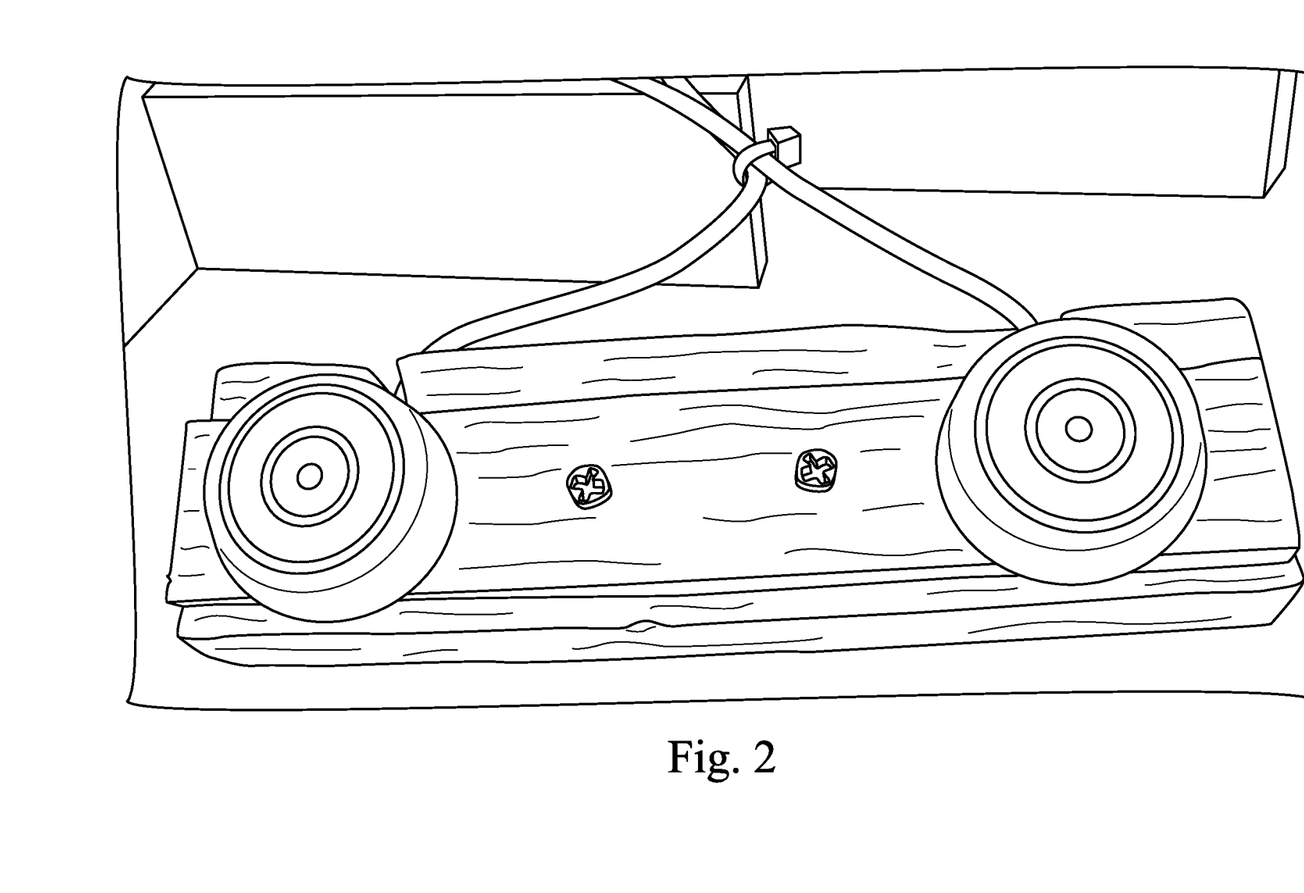
FIG. 2 is a photograph of a foot switch according to some embodiments of the invention.

FIG. 2 is a photograph of a foot switch, as an example of data input device 104, according to an embodiments of the invention. The foot switch comprises two buttons. During an examination, the examiner may step on the foot switch to record the response of the test human subject in identifying the visual target being displayed. For example, if the response is correct, the examiner may step on the right button. Likewise, if the response is incorrect, the examiner may step on the left button. Thus, the foot switch according to an embodiment of the invention allows the examiner to enter information concerning the subject's responses hands-free.

Head motion-inducing component 108 may be a mechanical device comprising a motor programmable to rotate the subject's head. Head motion-inducing component 108 may be controlled by data processor 103 via link 109. Head motion-inducing component 108, as an automatic device, may be desirable for home use.

Available commercial products from Micromedial Technologies and NeuroCom International only measure responses representing visual acuity during active, or self-induced, head motion. However, active head rotations allow the brain to use alternate, compensatory strategies to stabilize the eyes during head rotation and thus lead to a more functional measurement of the inner ear. The functional measurements, however, are not considered rigorous enough to discern pathology from compensation. In contrast, visual acuity test during passive, or externally induced, head rotation is a more physiologic assessment of the inner ear and may represent the standard way to measure inner ear balance function. Some embodiments of the invention allow, for the first time, a commercial product to perform visual acuity test during passive head rotation.

Some embodiments of the invention may comprise a computer-readable medium comprising software, when executed by a computer, causes the computer to receive a detected motion signal corresponding to a motion of a human subject's head from motion detector 102; cause a display device 101 to display a predetermined visual target based on the detected motion signal; receive information corresponding to a response of the human subject in identifying the predetermined visual target from data input device 104; and generate an output characterizing a gaze stability of said human subject.

Example computer-readable medium may include a CD-ROM, a DVD disk, a Blu Ray disk, a floppy disk, a magneto-optic disk, a magnetic tape, a flash drive, a hard disk drive, etc.

Figure 3:
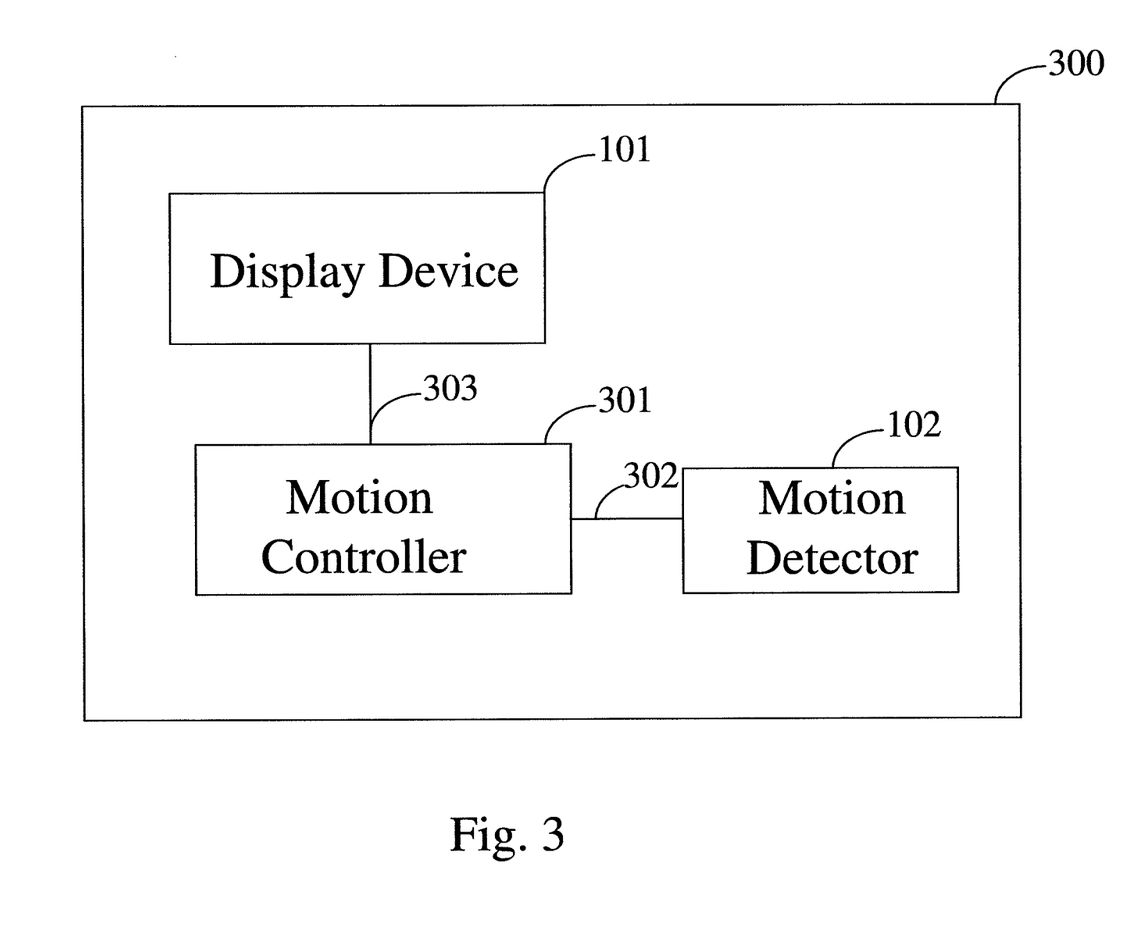
FIG. 3 is a schematic illustration of a system for training a subject to improve vestibular-ocular reflex (VOR) according to some embodiments of the invention.

FIG. 3 is a schematic illustration of a system for training a subject to improve vestibular-ocular reflex (VOR) according to some embodiments of the invention. A training system 300 comprises a display device 101, a motion controller 301, and a motion detector 102. Motion controller 301 is in communication with motion detector 102 and display device 101 via links 302 and 303, respectively. Links 302 and 303 may be wired or wireless, as discussed above in association with links 105 to 107 and 109.

Motion controller 301 may receive information encoding head motion velocity, via link 302, from motion detector 102 and configure, via link 303, display device 101 to display a visual target that moves in the opposite direction of the head motion. Motion controller 301 may be a computer that has at least one central processing unit (CPU), one memory, and one input/output (I/O) device. The computer may be programmed to run training exercises for the subject, for example, using the LabView programming language. Motion controller 301 may comprise an electro-mechanical device, for example, a galvanometer, to adjust the velocity of the moving visual target.

Figure 4:
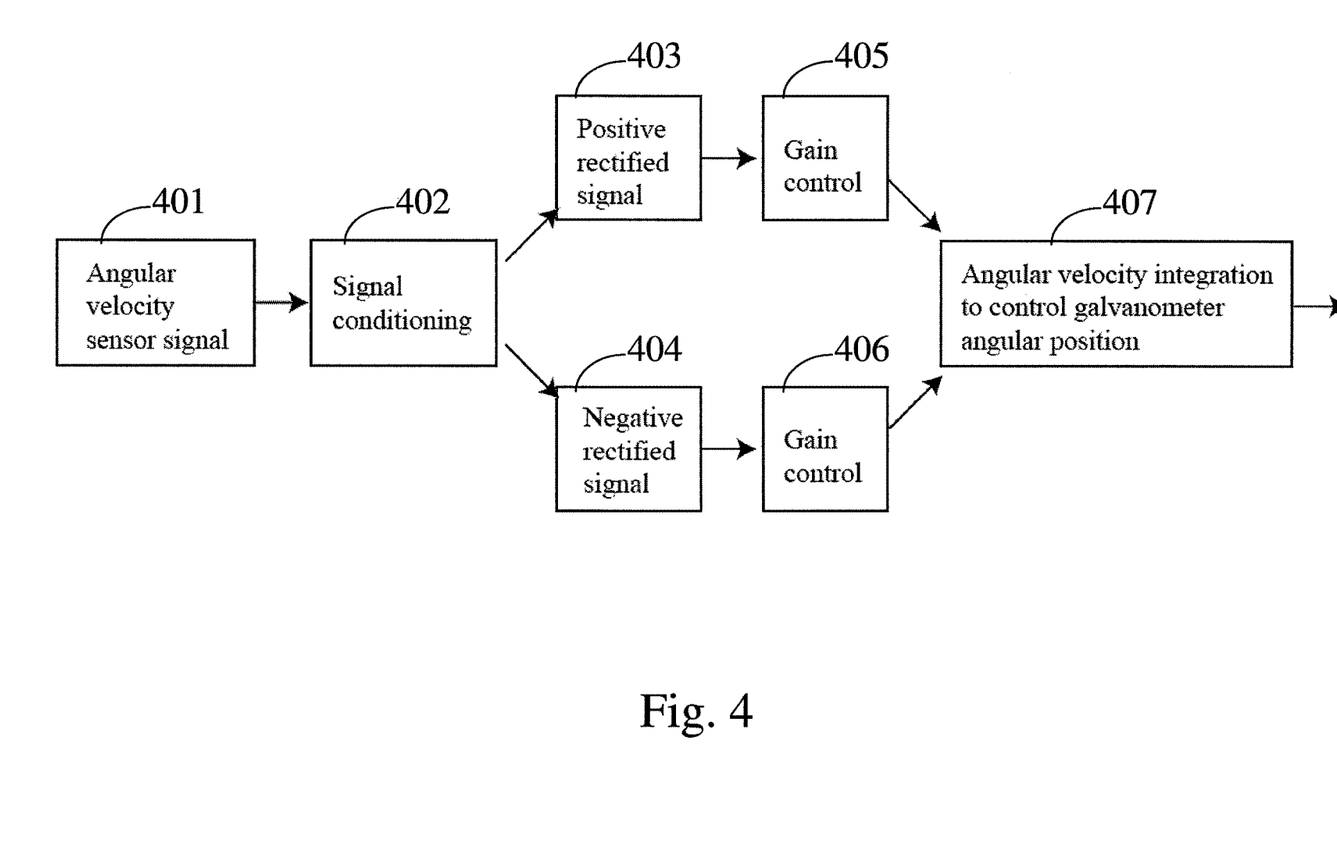
FIG. 4 is a flow chart of the angular velocity detection and integration according to some embodiments of the invention.

FIG. 4 shows a flow chart of the angular velocity detection and integration according to some embodiments of the invention. In block 401, an angular velocity sensor signal from motion detector 102 is received and passed to block 402 for signal conditioning, for example, removal of unwanted interfering signals. Positive rectified signal 403 undergoes gain control in block 405 while negative rectified signal 404 undergoes gain control in block 406. The gain control in blocks 405 and 406 may be individually adjusted. In block 407, the rectified angular velocity signal is integrated to control the galvanometer angular position.

Figure 5A:
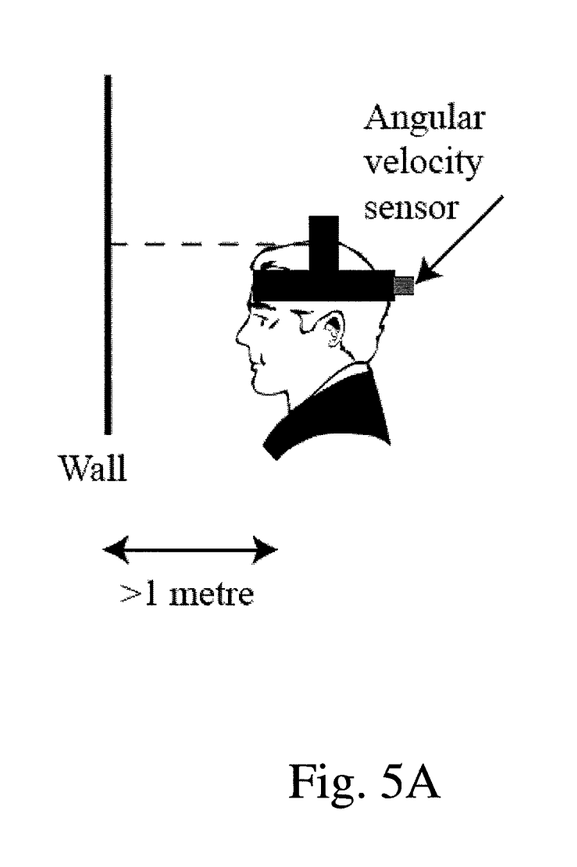
FIG. 5A is a schematic illustration of a motion detector mounted on a subject's head according to some embodiments of the invention.

FIG. 5A is a schematic illustration of a motion detector mounted in a head band according to some embodiments of the invention. The head band is worn by the subject staring at the wall. The distance between the wall and the motion detector is more than one meter.

Figure 5B:
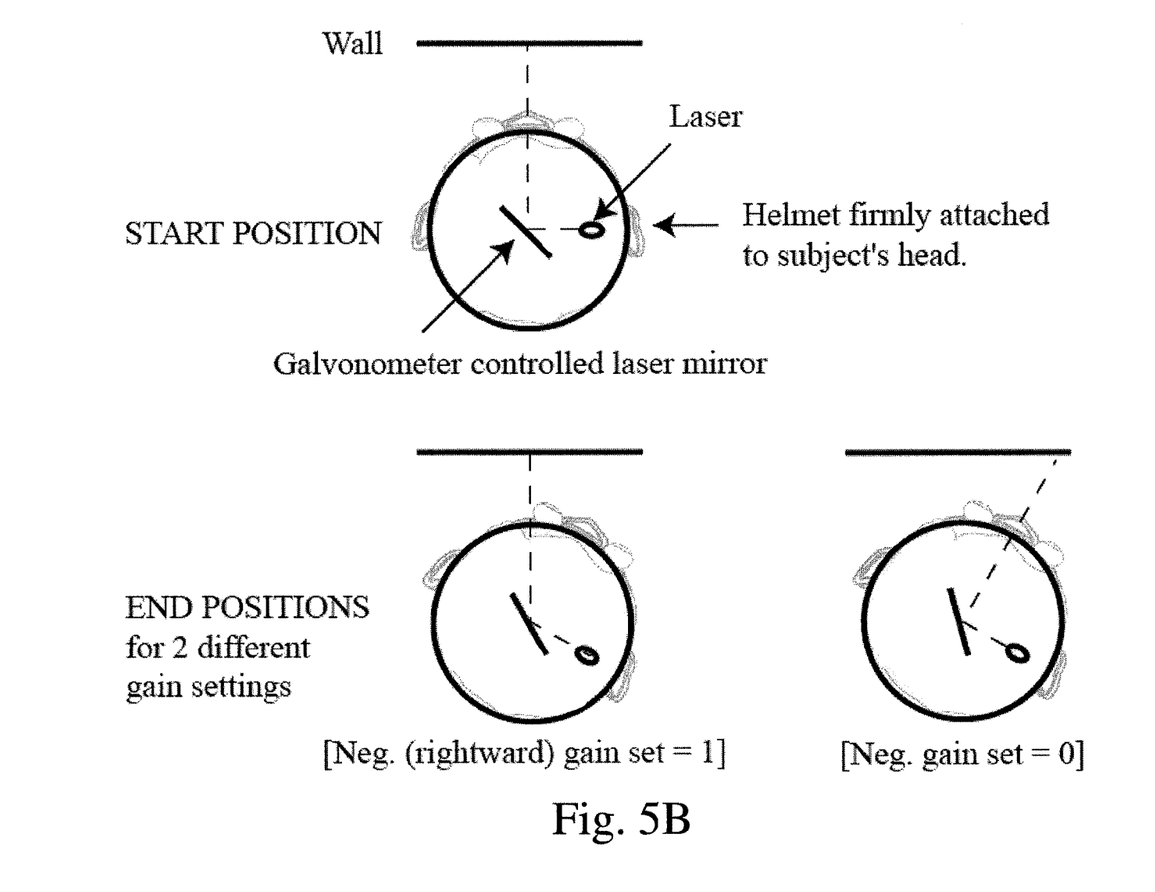
FIG. 5B shows diagrams of a galvanometer controlled laser projection display during a subject's head motion according to some embodiments of the invention.

FIG. 5B shows diagrams of a galvanometer controlled laser projection display during the subject's head motion according to some embodiments of the invention. The galvanometer controlled laser projection display is mounted in the same head band shown in FIG. 5A. When the subject's head turns rightward, the laser beam is rotated leftwards (by an amount depending on the preset gain) with respect to the head and vice versa. For example, in the starting position shown in FIG. 5B, a galvanometer controller laser mirror reflects a laser beam and projects it at the center of the wall in front of the human subject. After the subject's head turns rightward, the end position of the projected laser beam will depend on the gain control setting of the galvanometer. For example, if the gain setting is zero, then no compensation of head motion exists and the projected laser beam follows the head motion. If, however, the gain setting is negative unity, then the head motion is offset by the galvanometer laser mirror and the projected laser beam is still at the center of the wall.

Some embodiments of the invention may comprise a computer-readable medium, comprising software, which software when executed by a computer, causes the computer to receive from motion detector 102 data encoding a first velocity of a subject's head motion in a first direction; and cause display device 101 to display a visual target moving in a second direction, opposite to said first direction, and at a second velocity that is lower than said first velocity. The software may further cause the computer to gradually increase said second velocity of the visual target displayed by display device 101.

Figure 6:
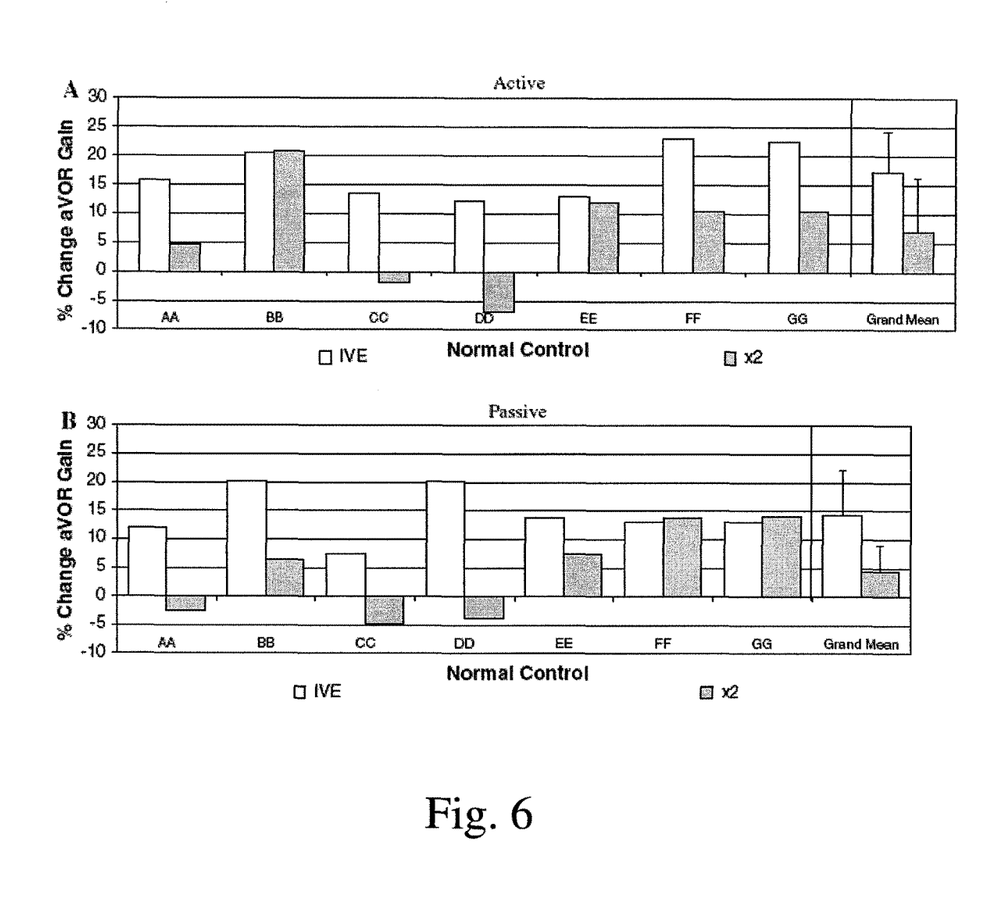
FIG. 6 shows the angular vestibulo-ocular reflex (aVOR) gain measured after training with active (self-induced) and passive (externally induced) head rotations for seven normal subjects according to some embodiments of the invention.

FIG. 6 shows the angular vestibulo-ocular reflex gain (aVOR) measured during active (self-induced) and passive (externally induced) head rotations after active head rotation training for seven normal subjects (AA through GG) according to some embodiments of the invention. The aVOR gain was calculated as a ratio of head and eye velocity measured during the experiments. Data from training under both the incremental (IVE) and x2 (same speed but in the opposite direction) is shown.

The aVOR gain change associated with the IVE training was demonstrated as larger than that associated with the x2 training for most subjects during both active (self-induced) and passive (externally induced) head rotations. The combined mean aVOR gain change for active (self-induced) head rotation was 17.3±4% and 7.1±9% (P=0.03) under the respective IVE and x2 training paradigms. For passive (externally induced) head rotation, the combined mean aVOR gain was 14.2±5% and 4.5±8% (P=0.02) under the respective IVE and x2 training paradigms. Two subjects (CC and DD) had no aVOR gain change following the x2 paradigm.

Figure 7:
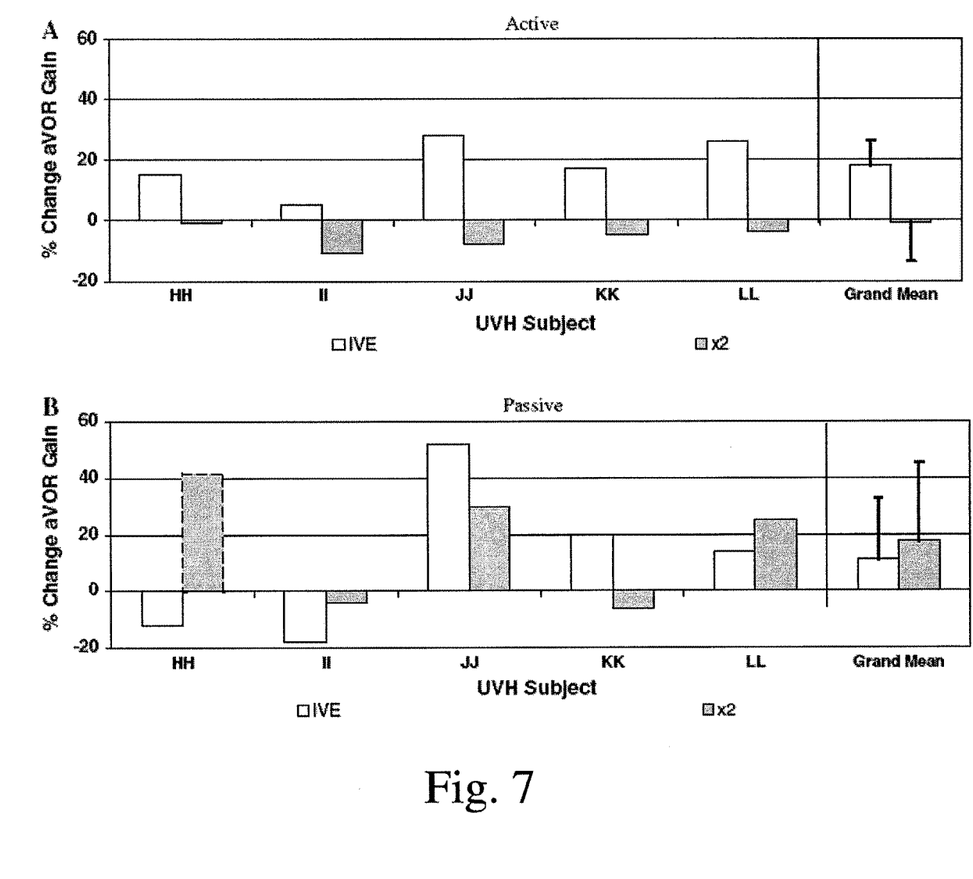
FIG. 7 shows the aVOR gain measured after training with active (self-induced) and passive (externally induced) ipsilesional head rotations for five unilateral vestibular hypofunction (UVH) subjects according to some embodiments of the invention.

FIG. 7 shows the aVOR gain measured during active (self-induced) and passive (externally induced) ipsilesional head rotations after active head rotation training for five unilateral vestibular hypofunction (UVH) subjects (HH through LL) according to some embodiments of the invention. Data from training under both the incremental (IVE) and x2 (same speed but in the opposite direction) paradigms is shown.

For active head rotations, all UVH subjects had greater mean aVOR gain change to ipsilesional head rotations after participation in the IVE paradigm (18±9.2%) compared with the x2 paradigm (~6±3.8%), (P<0.002). After participation in the IVE paradigm, four of five subjects had at least a 10% increase in aVOR gain, while one subject (II) demonstrated a more modest 5% increase, as shown in FIG. 7a. Therefore, although some variability exists in the amount of adaptation, the incremental paradigm appears to be superior in adapting the aVOR in patient subjects. For passive head rotations, there were no group differences between the IVE and x2 paradigms (MANOVA P>0.42), as shown in FIG. 7b.

According to a well established neurophysiologic principal, the brain has better memory retention when the subject is asked to make changes that are small and gradually applied compared with changes that are large and sudden. This principal was only recently found applicable for problems related to inner ear balance nerve damage. According to some embodiments of the invention, the brain can be trained to stabilize the eyes when it is exposed to visual targets that move at a progressively faster velocity relative to the head velocity. The incremental strategy adopted in some embodiments of the invention exposes the adaptive learning process of the brain to a signal that is small enough to appear permanent (possibly from a pathological condition) and therefore should be remembered. In comparison, the x2 strategy presents a disturbance that is likely to be interpreted as more transient, like an artificial external perturbation, and therefore not to be remembered.

The improvements observed after training according to some embodiments of the invention are not due to enhancement of the pursuit system. There is no evidence for the pursuit system being enhanced and the head velocities during training are above the known applicable range of enhanced smooth pursuit in bilateral vestibular hypofunction patients. Neither are these improvements attributable to the increased use of compensatory saccades or anticipatory eye rotations.

In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A system to improve vestibulo-ocular reflex (VOR), comprising a display device;

a head motion detector, said head motion detector configured to detect at least one of a first angular rotational rate of a subject's head or a first acceleration of said subject's head in a first direction;

a signal conditioner in communication with said head motion detector;

a first gain control in communication with said signal conditioner;

a second gain control in communication with said signal conditioner;

a motion controller in communication with said display device and said first gain control and said second gain control; and a head motion-inducing device configured to induce a head motion on said subject, wherein the head motion-inducing device includes a motor configured to rotate a head of the subject based on an instruction produced by a data processor, wherein said signal conditioner is adapted to:

remove interfering signals from head motion data, transmit a positive rectified signal to said first gain control, and transmit a negative rectified signal to said second gain control, wherein the first gain control and the second gain control are individually adjusted, said motion controller is adapted to receive information encoding the subject's head motion from said first gain control and said second gain control, and said motion controller is further adapted to control the display device to display a visual target to said subject such that said visual target moves in a second direction opposite to said first direction in correspondence with the subject's head motion.

2. The system of claim 1, wherein said display device is at least one of a cathode ray tube (CRT) monitor, a liquid crystal display (LCD) monitor, a digital light projection (DLP) monitor, a projector display, a laser projector, a plasma screen, an organic light emitting diode (OLED).

3. The system of claim 1, wherein said motion controller comprises a galvanometer.

4. The system of claim 1, wherein said motion controller is further adapted to adjust a velocity of said visual target displayed by said display device.

5. The system of claim 1, wherein said display device, head motion detector, and motion controller are adapted to be worn by the subject.

6. The system of claim 1, wherein the correspondence is a correspondence between a head motion velocity and a visual target velocity.

* * * * *